US005672659A

United States Patent [19]

Shalaby et al.

[11] Patent Number: 5,672,659
[45] Date of Patent: Sep. 30, 1997

[54] IONIC MOLECULAR CONJUGATES OF BIODEGRADABLE POLYESTERS AND BIOACTIVE POLYPEPTIDES

[75] Inventors: Shalaby W. Shalaby, Pendleton, S.C.; Steven A. Jackson, Holliston; Jacques-Pierre Moreau, Upton, both of Mass.

[73] Assignee: Kinerton Limited, Ireland

[21] Appl. No.: 464,735

[22] PCT Filed: Jan. 5, 1994

[86] PCT No.: PCT/US94/00148

§ 371 Date: Jun. 29, 1995

§ 102(e) Date: Jun. 29, 1995

[87] PCT Pub. No.: WO94/15587

PCT Pub. Date: Jul. 21, 1994

[30] Foreign Application Priority Data

Jan. 6, 1993 [IE] Ireland ................... 930005

[51] Int. Cl.$^6$ ............... A61K 9/16; A61K 9/52; A61K 37/02
[52] U.S. Cl. ............ 525/54.1; 514/2; 514/772.3; 514/772.6; 514/800; 514/806; 514/807; 514/808; 514/809; 514/963; 424/489; 424/497; 424/499; 435/180; 435/181; 435/182
[58] Field of Search ............ 525/54.1; 514/2, 514/772.3, 772.6, 800, 806, 807, 808, 809, 963; 424/489, 497, 499; 435/180, 181, 182; 436/531, 532, 533, 534

[56] References Cited

U.S. PATENT DOCUMENTS

| | | | |
|---|---|---|---|
| 4,356,166 | 10/1982 | Peterson et al. | 424/19 |
| 4,609,707 | 9/1986 | Nowinski et al. | 525/54.1 |
| 4,767,628 | 8/1988 | Hutchinson | 424/426 |
| 5,071,909 | 12/1991 | Pappin et al. | 525/54.1 |
| 5,162,505 | 11/1992 | Dean et al. | 530/391.5 |
| 5,476,653 | 12/1995 | Pitt et al. | 525/54.1 |

FOREIGN PATENT DOCUMENTS

| | | |
|---|---|---|
| 0 467 389 A2 | 1/1992 | European Pat. Off. |
| 0 483 429 A1 | 5/1992 | European Pat. Off. |
| WO 92/11844 | 7/1992 | WIPO |

OTHER PUBLICATIONS

Shah et al., "Poly (glycolic acid–co–DL–lactic acid): Diffusion or Degradation Controlled Drug Delivery?", Journal of Controlled Realeas, 18:261–270, 1992.

*Primary Examiner*—Nathan M. Nutter
*Attorney, Agent, or Firm*—Fish & Richardson P.C.; William E. McGowan

[57] ABSTRACT

A composition including a polyester containing one or more free COOH groups ionically conjugated with a bioactive polypeptide comprising at least one effective ionogenic amine, wherein the polyester contains a member selected from the group of L-lactic acid, D-lactic acid, DL-lactic acid, ε-caprolactone, p-dioxanone, ε-caprolic acid, alkylene oxalate, cycloalkylene oxalate, alkylene succinate, β-hydroxybutyrate, substituted or unsubstituted trimethylene carbonate, 1,5-dioxopan-2-one, 1,4-dioxepan-2-one, glycolide, glycolic acid, L-lactide, D-lactide, DL-lactide, meso-lactide, and any optically active isomers, racemates or copolymers thereof, and at least 50%, by weight, of the polypeptide present in the composition is ionically conjugated to said polyester.

32 Claims, 3 Drawing Sheets

Forms of Lactate/ Glycolate-Type Polymers of Polycarboxyiic Acid-Tipped Chains

LINEAR CHAINS

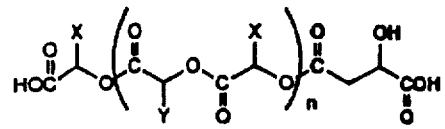

Di End Acid - Terminal Malic

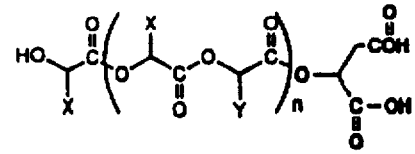

End Hydroxy - Terminal Malic

BRANCHED CHAINS

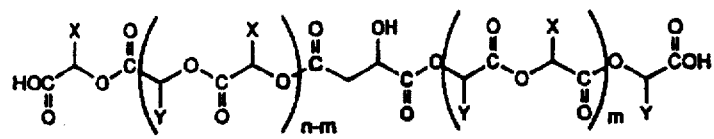

Di End Acid - Internal Malic

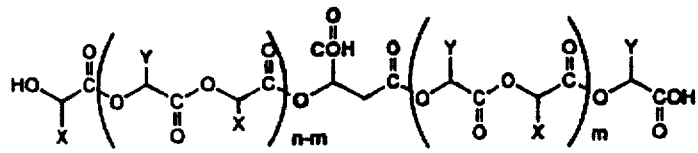

End Hydroxy - Internal Malic c) 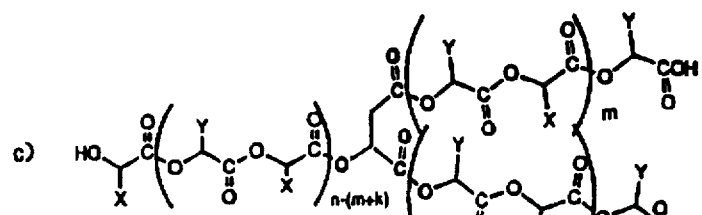

Fully Branched - Internal Malic

Y= CH$_3$ for Lactic, H for Glycolic; X= H for Glycolic, CH$_3$ for Lactic
Distribution of X + Y is formula dependent and polymerization dependent

FIG. 1

IONIC CONJUGATE EXAMPLE

IONIC MOLECULAR CONJUGATES OF BIODEGRADABLE POLYESTERS AND BIOACTIVE POLYPEPTIDES

RELATED APPLICATION DATA

This application is a national stage application filed under 35 USC 371 of PCT/US94/00148, filed Jan. 5, 1994.

BACKGROUND OF THE INVENTION

This invention pertains to sustained release of bioactive polypeptides.

Many drug delivery systems have been developed, tested and utilized for the controlled in vivo release of pharmaceutical compositions. For example, polyesters such as poly(DL-lactic acid), poly(glycolic acid), poly(ε-caprolactone) and various other copolymers have been used to release biologically active molecules such as protesterone; these have been in the form of microcapsules, films, or rods (Pitt C. G., Marks, T. A., and Schindler, A. 1980). Upon implantation of the polymer/therapeutic agent composition, for example subcutaneously or intramuscularly, the therapeutic agent is released over a specific period of time. Such biocompatible biodegradable polymeric systems are designed to permit the entrapped therapeutic agent to diffuse from the polymer matrix. Upon release of the therapeutic agent, the poller is degraded in vivo, obviating surgical removal of the implant. Although the factors that contribute to poller degradation are not well understood, it is believed that such degradation for polyesters may be regulated by the accessibility of ester linkages to non-enzymatic autocatalytic hydrolysis of the polymeric components.

Several EPO publications and U.S. Patents have addressed issues of polymer matrix design and its role in regulating the rate and extent of release of therapeutic agents in vivo.

For example, Deluca (EPO Publication 0 467 389 A2/Univ of Kentucky) describes a physical interaction between a hydrophobic biodegradable polymer and a protein or polypeptide. The composition formed was a mixture of a therapeutic agent and a hydrophobic polymer that sustained its diffusional release from the matrix after introduction into a subject.

Hutchinson (U.S. Pat. No. 4,767,628/ICI) controlled the release of a therapeutic agent by uniform dispersion in a polymeric device. It is stated that this formulation provides for controlled continuous release by the overlap of two phases: first, a diffusion-dependent leaching of the drug from the surface of the formulation; and second, releasing by aqueous channels induced by degradation of the polymer.

SUMMARY OF THE INVENTION

In general, the invention features a sustained release pharmaceutical formulation composed of a polyester containing one or more free COOH groups ionically conjugated with a biologically active polypeptide composed of at least one effective, ionogenic amine wherein at least 50%, by weight, of the polypeptide present in the composition is ionically conjugated to the polyester.

In preferred embodiments, the polyester is modified to increase the carboxyl to hydroxyl end group ratio from more than one and approaches infinity, i.e., all of the hydroxyl groups can be substituted with carboxyls. Examples of suitable polyesters are those originating from compounds such as L-lactic acid, D-lactic acid, DL-lactic acid, ε-caprolactone, p-dioxanone, ε-caproic acid, substituted and unsubstituted trimethylene carbonate, 1,5-dioxepan-2-one, 1,4-dioxepan-2-one, glycolide, glycolic acid, L-lactide, D-lactide, DL-lactide, meso-lactide, alkylene oxalate, cycloalkylene oxalate, alkylene succinate, (β-hydroxybutyrate), and optically active isomers, racemates or copolymers of any of the above. Other heterochain polymers related to traditional polyesters may also be used (e.g., polyorthoesters, polyorthocarbonates, and polyacetals).

Preferably, the polyester is made polycarboxylic by reaction with malic acid or citric acid.

In preferred embodiments the polyester is partially acid-tipped with glutaric anhydride. In yet other preferred embodiments the polyester is fully acid-tipped with glutaric anhydride. Preferably, the polyester has an average degree of polymerization between 10 and 300 and more preferably between 20 to 50.

The ionic molecular conjugates of the invention are preferably made from polycarboxylic acid-tipped polyesters conjugated with monobasic and polybasic bioactive polypeptides having at least one effective ionogenic amine group. Alternatively, any polyester may be used to form an ionic molecular conjugate of the invention provided it is pretreated with a suitable base, e.g., NaOH. Moreover, any acid-stable peptide can be used, e.g., growth hormone releasing peptide (GHRP), luteinizing hormone-releasing hormone (LHRH), somatostatin, bombesin, gastrin releasing peptide (GRP), calcitonin, bradykinin, galanin, melanocyte stimulating hormone (MSH), growth hormone releasing factor (GRF), amylin, tachykinins, secretin, parathyroid hormone (PTH), enkaphelin, endothelin, calcitonin gene releasing peptide (CGRP), neuromedins, parathyroid hormone related protein (PTHrP), glucagon, neurotensin, adrenocorticothrophic hormone (ACTH), peptide YY (PYY), glucagon releasing peptide (GLP), vasoactive intestinal peptide (VIP), pituitary adenylate cyclase activating peptide (PACAP), motilin, substance P, neuropeptide Y (NPY), TSH, and analogs and fragments thereof. Such ionic molecular conjugates are capable of releasing their bioactive components in vivo at predetermined rates determined by the chemical structure, molecular weight, and pKa of both components of these conjugates. A mechanism for the release of the drug entails the transformation of the insoluble conjugate form to water-soluble components, in part, through the hydrolysis of the hydrophobic polyester. Thus, release of the bioactive polypeptide increases, independently, with (a) the decrease in the pKa differential between the bioactive polypeptide and polyester, (b) the chemical reactivity of the polyester chain that is reflected in the carbonyl nucleophilicity, (c) the decrease in polyester density, as it relates to the glass transition temperature and minimized crystallizability, and (d) the increase in matrix hydrophilicity.

In preferred embodiments the polypeptide comprises 1 to 50 percent by weight of the total weight of the ionic molecular conjugate, and preferably greater than 85%, more preferably 95%, and even more preferably 99%, of the polypeptide present in the composition is ionically conjugated to the polyester; the polyester component of the ionic molecular conjugate has a viscosity of about 0.05 to about 0.7 dl/gm in chloroform; and the polyester has an average molecular weight of about 1200–40,000.

The polymeric ionic molecular conjugates of the invention can easily be made into injectable microspheres or microparticles, and implantable films or rods, without the need to utilize processing that entails multiphase emulsions or non-aqueous two-phase systems. Preferably, the microparticles are manufactured by (a) dissolving the composition in an aprotic, water miscible organic solvent; (b) mixing the organic solvent in water; and (c) isolating the microparticles from the water. In preferred embodiments, the organic solvent is chosen from the group of acetone, acetonitrile, tetrahydrofuran, dimethylformamide, and dimethoxy ethylene glycol.

In preferred embodiments the polyester/polypeptide ionic molecular conjugate is capable of releasing in vivo a therapeutically effective dose of a bioactive polypeptide over a period of at least 20 days, and more preferably for up to 95 days but not less than 7 days. In yet other preferred embodiments the release of the therapeutic ionic molecular conjugate is essentially monophasic.

The sustained release compositions of the invention are preferably made by (a) providing a polyester having free COOH groups and a bioactive polypeptide having at least one effective ionogenic amine, and (b) ionically conjugating the polyester to the polypeptide to form an ionic molecular conjugate, wherein at least 85%, by weight, of the polypeptide present in the composition is ionically conjugated to the polyester. The polyester can be one which has sufficient free COOH groups to begin with, or, if an insufficient number of such groups are available for the desired peptide loading level at the outset, the polyester can be (1) reacted with, e.g., malic or citric acid through esterification or functional interchange, or (2) acid-tipped with, e.g., glutaric anhydride or (3) the polyester can be treated with a base, e.g., NaOH, to expose acid groups. Finally, the polyester/polypeptide ionic molecular conjugate may be converted to implantable films or rods, or injectable microspheres or microparticles capable of releasing in vivo the polypeptide.

Preferably, the polyester is synthesized by catalyzing or autocatalyzing direct condensation of one or more hydroxy acids, e.g., glycolic acid and lactic acid, in the presence of a predetermined concentration of a polycarboxylic hydroxy acid, e.g., malic acid or citric acid. The polyesters thus formed possess acid-tipped hydroxyl end groups which are preferably partially or fully acid-tipped.

The polyesters also can be synthesized by catalyzing ring-opening polymerization of lactones, or by polymerization of cyclic monomers such as ε-caprolactone, p-dioxanone, trimethylene carbonate, 1,5-dioxepan-2-one, or, 1,4-dioxepan-2-one in the presence of a chain initiator, e.g., a hydroxy polycarboxylic acid.

Another method of synthesizing involves reacting a hydroxy acid with a cyclic dimer, followed by condensation of the open chain system in the presence of a polycarboxylic acid.

Yet another synthetic method involves reacting an organic polycarboxylic acid with a preformed polyester.

In the aforementioned preferred embodiments the acid-tipped polyester has a carboxyl to hydroxyl end group ratio of more than one and approaching infinity (i.e., eliminating all the hydroxyl groups) with an average degree of polymerization between 10 and 300, and in particularly preferred embodiments between 20 and 50.

Alternatively, a polyester is rendered capable of forming an ionic molecular conjugate with a bioactive polypeptide by treatment with a base, e.g., NaOH.

Preferably, the polyester/polypeptide ionic molecular conjugate is synthesized by direct interaction between the polyester, e.g., in the free form, and the polypeptide, e.g., in the free form, in the proper liquid medium. In other preferred embodiments suitable solvents for the formation of the conjugate would be a mixture aprotic solvent [e.g., acetone, tetrahydrofuran (THF), or ethylene glycol dimethylether] and a suitable solvent for the peptide (e.g., water) in proportions such that the two systems are miscible. Preferably, the polypeptide is a salt of a monocarboxylic acid having a pKa greater than or equal to 3.5. Preferably, the polypeptide has at least one effective ionogenic amine group.

In preferred embodiments the polypeptide is 1 to 50 percent by weight, and preferably 10 to 20 percent of the polyester/polypeptide ionic molecular conjugate. In preferred embodiments, the accessible carboxyl groups of the polyester are partially neutralized with alkali metal ions or organic bases. In yet other preferred embodiments, the alkali treatment provides chain dissociation of the polyester and formation of lower molecular weight binding sites.

"Polypeptide", as used herein, refers to a protein, peptide, oligopeptide or synthetic oligopeptide.

"Polycarboxylic", as used herein, refers to compounds having more than one carboxyl group, e.g., malic acid and citric acid.

"Average degree of polymerization", as used herein, refers to the number of repeat monomer sequences.

"Effective ionogenic amine", as used herein, refers to a polypeptide that contains at least one amine group capable of forming an ion under prevailing conditions.

"Acid-tipped", as used herein, refers to compounds having an acid terminus.

"Partially acid-tipped", as used herein, refers to compounds having 1–99 percent of their hydroxyl end groups acid-tipped.

"Fully acid-tipped", as used herein, refers to compounds having greater than 99.9% of their hydroxyl groups acid-tipped.

"Hydroxy acids", as used herein, refers to any compound containing hydroxyl and carboxyl groups.

"Monocarboxylic hydroxy acid", as used herein, refers to an organic acid with one carboxyl group and one or more hydroxyl group.

"Polycarboxylic hydroxy acid", as used herein, refers to a hydroxy acid with more than one carboxyl group.

"Organic entrainer", as used herein, refers to organic liquids which codistill with water.

"Bioactive", as used herein, refers to a molecule that elicits or affects a biological event.

"Acyclize", as used herein, refers to a chemical reaction that occurs by ring opening.

"Polycondensation", as used herein, refers to the formation of a polyester by the condensation of two or more molecules.

The present invention provides a new pharmaceutical composition that chemically bonds a biocompatible, biodegradable polyester to oligopeptides, polypeptides, peptides and or proteins as a homogeneous ionic species. By chemically bonding polyesters of different molecular weights to the therapeutic agents, the chemical characteristics of the composition can be more precisely tailored to meet the demands for the controlled monophasic release of the biologically active polypeptide molecule in vivo. Furthermore, the compositions of the invention are optimized easily to possess functional properties for greater loading of a therapeutically active polypeptide.

Other features and advantages of the invention will be apparent from the following detailed description of the preferred embodiments, and from the claims.

BRIEF DESCRIPTION OF THE DRAWINGS

FIG. 1 is an illustration representing isomers of polycarboxylic acid-tipped lactide/glycolide (malic type) copolymer.

DESCRIPTION OF THE PREFERRED EMBODIMENTS SYNTHESIS

Figure 2:
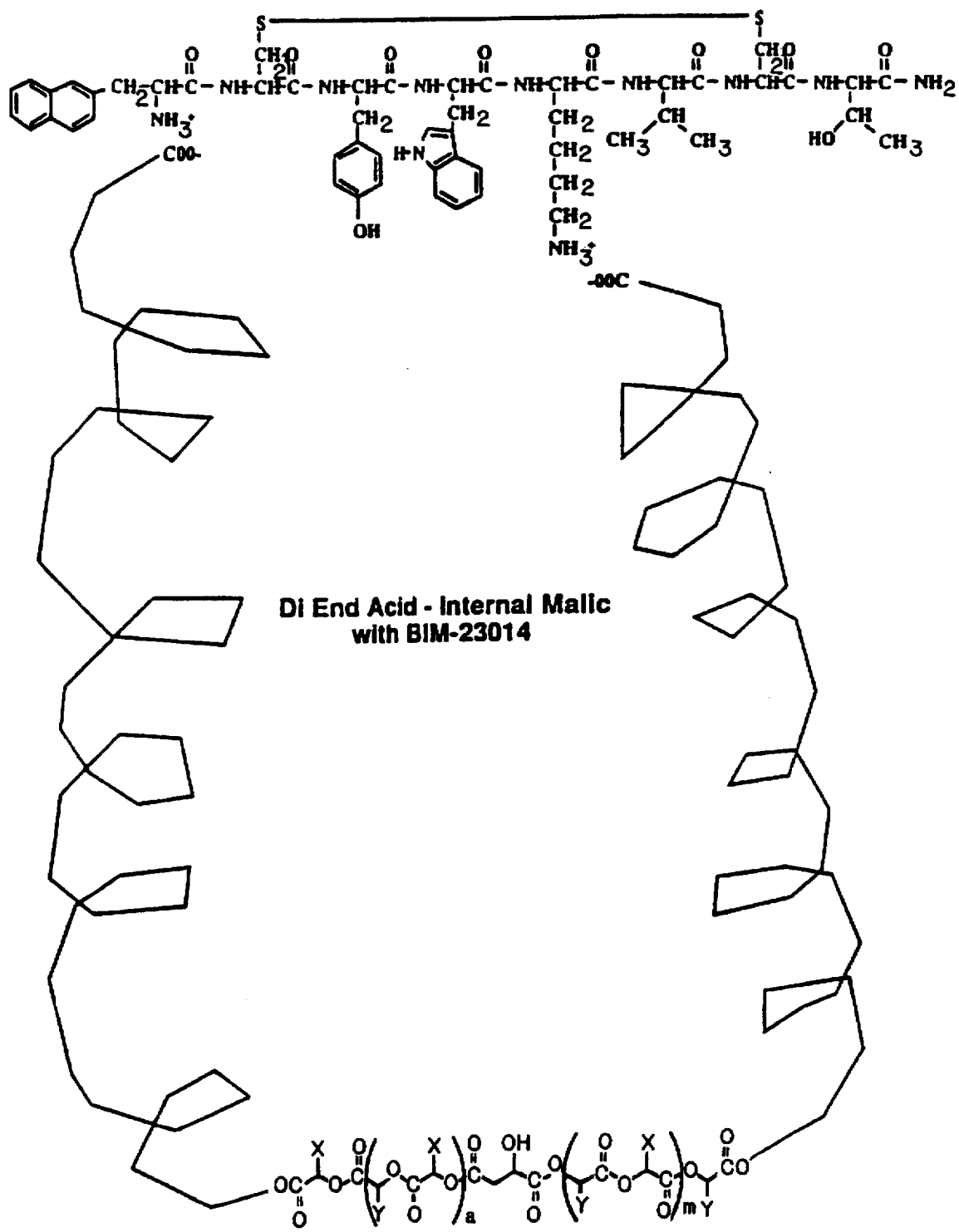
FIG. 2 is an illustration of an ionic molecular conjugate depicting the chemical interactions between the lactide/glycolide (malic type) copolymer and Somatuline (BIM-23014).

The biodegradable or absorbable polyesters of the invention are tailored to possess the desired chemical reactivity to provide controlled chain hydrolyzability and exhibit maximum binding capacity to oligopeptides, polypeptides or proteins having a net positive charge at physiologic pH, by the proper selection of the constituent monomers, co-monomers or comers to form chains with predetermined compositions and molecular weights (see, e.g. FIG. 2).

A tripartite synthetic design, within the ability of someone of ordinary skill in this field, is employed to prepare the compositions of the present invention. The steps include: (1) synthesis of the polycarboxylic acid-tipped polyesters; (2) synthesis of the polyester/polypeptide ionic conjugate by ionic interaction of polycarboxylic acid-tipped polyesters (or a polyester treated with a base) and biologically active polypeptides; and (3) conversion of ionic conjugates to implants, rods, microspheres or microparticles capable of releasing in vivo the therapeutic agent for at least 7 days.

1) Synthesis of polycarboxlic acid-tipped polyesters.

The polycarboxylic acid-tipped polyester chains of the invention are synthesized by methods such as direct condensation of a 2-hydroxy acid and a polycarboxylic organic acid, step-growth polymerization of acyclized products, ring-opening polymerization of a lactone or a lactone mixture, or functional interchange of a polycarboxylic organic acid with preformed high molecular weight polyesters (See FIG. 1) Descriptions of the synthesis of polycarboxylic acid-tipped polyesters by these aforementioned methods follow.

Direct condensation of 2-hydroxy acids in an optically active and/or an inactive form and a predetermined amount of a polycarboxlic organic acid in the presence or absence of inorganic, or organometallic catalyst, e.g., condensation of glycolic acid DL-lactic acid, and DL-malic acid is generally accomplished by heating the monocarboxylic hydroxy acids or mixture of two or more monocarboxylic hydroxy acid in the presence of a fraction of polycarboxylic hydroxy acid in a glass reactor equipped for providing a continuous flow of dry-nitrogen and mass agitation (designated Type IA Polyester, see Table I). Typically, the polycondensation is conducted at 150°–170° C. for 4 to 72 hours. Agitation of the reaction mixture can be provided by a magnetic stirrer or bubbling the nitrogen gas through the polyester mass. The polymerization is continued until the desired average molecular weight (determined in terms of solution viscosity) and/or acid number (determined by end group titration) is achieved. Polyester analysis by end group titration is performed as follows. Polyester samples (300 mg–500 mg) are accurately weighed and dissolved in a minimal amount (10–30 ml) of acetone. After dissolution, the solutions are diluted to 100 ml with benzyl alcohol (Mallinckrodt, Analytical Reagent) and titrated to a faint pink end-point (phenolphthalein) using potassium hydroxide in benzyl alcohol solution (Normalized vs. HCl Standard). The volume of base solution used for the sample ($\Delta Vs$) is compared with the volume of base used for a solvent blank ($\Delta Vo$) to determine the acid number for the polyester.

$$\text{Acid \#} = \frac{\text{Wt. of Sample (mg)}}{\{\Delta Vs(\text{ml}) - \Delta Vo(\text{ml})\}} \times N \text{ of Base}$$

At the conclusion of polymerization, the polyester is isolated and extracted with water or a dilute aqueous sodium hydroxide solution, from a suitable organic solution to remove water-soluble or solubilizable low molecular weight chains.

Polyester analysis by GPC is performed as follows. The average molecular weights (MW) of polyester were determined by GPC using a Waters Model 6000 solvent delivery pump and a Dynamax (Rainin) model UV-D detector. Runs were performed in tetrahydrofuran (Burdick & Jackson UV grade) using a Jordin Gel DVB 1000 Å, 50 cm×10 mm column (Jordi Associates) at a flow rate of 1.2 ml/min at 25 C. Peak detection was at 220 nm and 1.0 AUFS. The column was calibrated using narrow band polystyrene reference standards (Polysciences Inc.) at Mw=4000, 9,200 and 25,000.

A modification of the direct condensation process entails the use of an organic entrainer and a cationic exchange resin as a condensation catalyst (designated Type IB Polyester, see Table I). This process requires a filtration and evaporation step to remove the catalyst and entrainer, respectively. Typical examples of polyesters made by these processes and pertinent analytical data are described in Table I.

TABLE I

POLYESTERS MADE BY DIRECT CONDENSATION METHOD

| Polymer # | | Charge | Polymerization Conditions | Acid # | $\eta_{inh}$ | Tg, °C. |
|---|---|---|---|---|---|---|
| | | Type IA Polyesters | | | | |
| 1 | L-Lactic Acid (88%) | 35.7 gm (0.349M) | 100° C./0.7 hr | 563 | 0.24 | 11 |
| | Glycolic Acid | 4.65 gm (0.612M) | 165° C./17.5 hrs | | | |
| | Citric Acid | 1.75 gm (0.0091M) | | | | |
| 2 | L-Lactic Acid (88%) | 25.6 gm (0.25M) | 165° C./22 hrs | 820 | 0.14 | 27 |
| | Glycolic Acid | 19.2 gm (0.25M) | | | | |
| | Malic Acid | 1.5 gm (0.011M) | | | | |

TABLE I-continued

POLYESTERS MADE BY DIRECT CONDENSATION METHOD

| Polymer # | Charge | | Polymerization Conditions | Acid # | $\eta_{inh}$ | Tg, °C. |
|---|---|---|---|---|---|---|
| | | Type IB Polyesters | | | | |
| 3 | L-LActic Acid (88%) | 25.6 gm (0.25M) | 132° C./53 hrs | 842 | 0.11 | 15 |
| | Glycolic Acid | 19.2 gm (0.25M) | | | | |
| | Citric Acid | 2.13 gm (0.011M) | Using Dean-Stark | | | |
| | Amberlyst | 0.5 gm | Trap. Decanted, | | | |
| | Catalyst Beads #15 | | filtered in | | | |
| | Toluene | 150 ml | Acetone. Dried. Washed with water. Vacuum dried. | | | |
| 4 | L-Lactic Acid (88%) | 25.6 gm (0.25M) | 132° C./68 hrs | 1421 | 0.20 | 28 |
| | Glycolic Acid | 19.2 gm (0.25M) | | | | |
| | Malic Acid | 1.5 gM (0.011M) | Using Dean-Stark | | | |
| | Amberlyst | | Trap. Decanted, | | | |
| | Toluene | 100 ml | Filtered, Dried. Washed with water and Vacuum Dried. | | | |

*Determined on a differential scanning calorimeter (TA 2100 DSC) using 2–10 mg sample heating rate of 10° C./min in a nitrogen atmosphere Step-growth polymerization of acyclized products, where a hydroxy acid is allowed to react with cyclic dimers and subsequent condensation of the resulting open chain system in the presence of predetermined amounts of a polycarboxylic acid and the presence or absence of a suitable condensation catalyst e.g. glycolic acid, L-lactide and DL-malic acid, essentially the same as the condensation process described above, except that it employs a mixture of a monocarboxylic hydroxy-acid, a cyclic dimer of a second hydroxy-acid, and a hydroxy polycarboxylic acid. Examples of polyesters made by this process and pertinent analytical data are summarized in Table II. When the cyclic dimer is pretreated with water the system is treated as a simple step-growth polymerization.

toluene), which are transferred under a dry oxygen-free atmosphere into a glass reactor equipped for magnetic or mechanical stirring. The polymerization reaction is continued under nitrogen following a suitable heating scheme until the desired molecular weight is achieved (as measured in terms of solution viscosity). At the conclusion of the polymerization scheme, the temperature is lowered and the unreacted monomer is distilled under reduced pressure. The polyester mass is then cooled and the water-soluble low molecular weight fractions are removed by low temperature extraction from a suitable organic solution. The solution is then dried and the solvent is removed. The molecular weight is then determined in terms of inherent viscosity and the acid number is determined by end-group titration. Examples of

TABLE II

STEP-GROWTH POLYMERIZATION OF ACYCLIZED PRODUCTS

| Polymer # | Charge | | Polymerization Conditions | Acid # | $\eta_{inh}$ | Tg, °C.* |
|---|---|---|---|---|---|---|
| | | Type II Polyesters | | | | |
| 1 | L-Lactide Monomer | 10.0 gm (0.07M) | 160° C./29 hrs | 1200 | 0.21 | 20 |
| | Glycolic Acid | 10.7 gm (0.14M) | Malic Acid | | | |
| | | 0.79 gm (0.0061M) | | | | |
| 2 | L-Lactide Monomer | 20.0 gm (0.139M) | 25° C.–155° C./1.5 h | 1800 | 0.13 | 27 |
| | Glycolic Acid | 7.1 gm (0.093M) | 155° C./70 hr | | | |
| | Malic Acid | 1.01 gm (0.007M) | Dissolve in DCM wash with water, and dry in vacuo. | | | |

*Determined on a differential scanning calorimeter (TA2100 DSC) using 2–10 mg sample and heating rate of 10° C./min in a nitrogen atmosphere Ring opening polymerization of a lactone or lactone mixture in the presence of a predetermined concentration of hydroxy-polycarboxylic acid as a chain initiator and a catalytic amount of an organometallic catalyst e.g. a mixture of L-lactide, glycolide and DL-malic acid in the presence of stannous octoate employs dry cyclic monomers or a mixture of cyclic monomers, a hydroxy-polycarboxylic acid and a trace amount of stannous octoate (used as 0.33M solution in polyesters prepared by this process and pertinent analytical data are given in Table III.

TABLE III

POLYESTERS MADE BY RING OPENING POLYMERIZATION

| Polymer # | Charge | | Polymerization Conditions | Acid # | $\eta_{inh}$ | Tg, °C.* |
|---|---|---|---|---|---|---|
| Type III Polyesters | | | | | | |
| 1 | Glycolide | 3.22 gm (0.028M) | 120° C./0.5 hr | 2,150 | 0.79 | 38 |
|   | L-Lactide | 10.7 gm (0.14M) | 150° C./6 hrs | | | |
|   | Malic Acid | 0.79 gm (0.0061M) | 120° C./11 hrs | | | |
| 2 | Glycolide | 2.84 gm (0.245M) | 120° C./0.5 hr | 1,206 | 0.08 | 26 |
|   | D,L-Lactide | 20.0 gm (0.139M) | 180° C./2.5 hrs | | | |
|   | Malic Acid | 0.876 gm (0.00541M) | 130° C./15 hrs | | | |
| 3 | Glycolide | 2.84 gm (0.0245M) | 155° C./1 hr | 937 | 0.10 | 27 |
|   | D,L-Lactide | 20.0 gm (0.139M) | 185° C./2.5 hrs | | | |
|   | Citric Acid | 1.256 gm (0.00654M) | 190° C./2.5 hrs | | | |
|   | | | 160° C./13 hrs | | | |
| 4 | Glycolide | 8.06 gm (0.0694M) | 180° C./1 hr | 970 | 0.26 | 23 |
|   | D,L-Lactide | 10.0 gm (0.0694M) | 185° C./2 hrs | | | |
|   | Malic Acid | 0.744 gm (0.00555M) | 195° C./7 hrs | | | |
|   | | | 120° C./9 hrs | | | |
| 5 | Glycolide | 8.06 gm (0.0694M) | 150° C./0.5 hr | 10,138 | 0.39 | 30 |
|   | D,L-Lactide | 10.0 gm (0.0694M) | 185° C./4 hrs | | | |
|   | 1,6-hexanediol | 0.656 gm (0.00555M) | 150° C./1.5 hrs | | | |
|   | | | 120° C./3 hrs | | | |

*Determined on a differential scanning calorimeter (TA2100 DSC) using 2-10 mg sample and heating rate of 10° C./min in a nitrogen atmosphere
**In hexofluoroisopropanol Functional interchange of polycarboxlic or hydroxypolybasic organic acid with preformed high molecular weight polyesters with COOH/OH ratio of unity to virtually zero, preferably in the presence of an organometallic catalyst, e.g. melt-reaction of an 85/15 lactide/glycolide copolymer with a molecular weight greater than 5,000 and COOH/OH≦1 with DL-malic acid in the presence of stannous octoate, to produce the lower molecular weight polyesters with COOH/OH≧1, entails heating a high molecular weight polyester with a predetermined amount of polycarboxylic or hydroxypolycarboxylic acid in the presence of a trace amount an organometallic catalyst such as stannous octoate. The reactants are heated above 150° C. under dry nitrogen with intensive agitation until the functional interchange is completed (as measured by depletion of residual unreacted polycarboxylic acid). In effect this is determined by monitoring the molecular weight (in terms of solution viscosity using capillary viscometry at 28° C.) of the resultant lower molecular weight polyester and the presence of unreacted polycarboxylic acid. This is achieved by aqueous extraction of a polyester sample and analysis of the extract using high performance liquid chromatography (HPLC). Residual monomer, dimer and polycarboxylic acid levels were determined by HPLC using a Waters Model 6000 solvent delivery pump and a Dynamax (Rainin) model UV-D detector (205 nm, 1.0 AUFS). Runs were performed using 0.025N $Na_2PO_4$ buffer, pH=3.5 (isocratic flow rate=1.0 ml/min.) using a Nucleosil C18, 5 um, 25 cm×4.6 mm column.

The desired polyester is isolated and purified as described above for ring-opening polymerization. An example of a polyester made by this process and pertinent analytical data are given in Table IV.

TABLE IV

POLYESTERS MADE BY FUNCTIONAL INTERCHANGE

| Polymer # | Charge | | Polymerization Conditions | Acid # | $\eta_{inh}$ | Tg, °C. |
|---|---|---|---|---|---|---|
| Type IV Polyesters | | | | | | |
| 1 | Boehringer A001 | 8 gm (50/50 dl-Lactide/Glycolide) | 150° C./5 hrs | 670 | 0.26 | 25 |
|   | Citric Acid** | 0.8 gm (0.00417M) | | | | |

*Determined on a differential scanning calorimeter (TA2100 DSC) using 2-10 mg sample and heating rate of 10° C./min in a nitrogen atmosphere
**A catalytic amount of stannous octoate (2 drops of 0.33 M solution, approximately 0.03 nmole).

Among the other monomers suitable for the synthesis of the polyesters used in the invention are: L-lactic acid, DL-lactic acid, ε-caprolactone, p-dioxanone, ε-caproic acid, trimethylene carbonate, 1,5-dioxepan-2-one, 1,4-dioxepan-2-one, glycolide, and meso-lactide. Examples of a useful polycarboxylic chain initiators and/or chain modifiers include malic acid, and citric acid.

(2) Synthesis of the polyester/polypeptide ionic conjugate by ionic interaction of polycarboxylic tipped polyesters and biologically active polypeptides. The polycarboxylic acid-tipped biodegradable polyesters described above are used to make an ionic molecular conjugates with mono- or polycarboxylic oligopeptides, polypeptides or proteins with accessible effective ionogenic amine groups (see FIG. 2). Moreover, any polyester is rendered capable of forming an ionic molecular conjugate with a polypeptide provided it is treated with a base, e.g., 0.1N NaOH. Such treatment exposes acid groups of the polyester for multiple site ionic interaction with the cationic polypeptide.

Thus, the formation of these conjugates is achieved by direct molecular interaction of the components in the proper solvent with or without a pretreatment of the polyester with an inorganic base to maximize its binding rate capacity to the basic drug. As noted above, the ionic interaction of their ionic conjugate components increases within the difference in their pKa values.

The polyester is dissolved in a suitable aprotic solvent in a concentration range of 2% to 20% W/V. Such solvents should dissolve the polyesters, but also be partly miscible with water. Suitable solvents used for this purpose include tetrahydrofuran, acetone, and ethylene glycol dimethylether. To this solution, an aqueous solution of base such as sodium, potassium or ammonium hydroxide or carbonate is added to maximize the binding capacity of the polyester. In general, the amount of base added corresponds to the amount of acid represented by the counter-anion level of the basic peptide to be used.

After briefly mixing the polyester-base combination, an aqueous solution of peptide or peptide salt is added at peptide/polyester loading levels of 2% to 50% W/W (peptide/polyester). This mixture is stirred for a period of time (up to 3 hours), and then the solvents are removed and the product is dried under vacuum. The resulting material may then be further processed for dosage formulation. The resulting pharmaceutical compositions are designed to be chemically uniform compositions made totally of ionic molecular conjugates and are essentially devoid of microscopically or macroscopically dispersed domains of the active drug in the biodegradable matrix. Examples of prepared ionic molecular conjugates and pertinent analytical data are given in Table V.

TABLE V

IONIC MOLECULAR CONJUGATE-PEPTIDE BINDING[1]

| | Polymer Used | Peptide[2] | Loading % | Retention[3] % |
|---|---|---|---|---|
| 1 | 50/50 dl Lactide/Glycolide (Commercial) Acid # = 22,000 $\eta_{inh} = 0.53$ | I I II III | 10 20 20 20 | 47 25 73 48.5 |
| 2 | Poly L-Lactide (Commercial) Mw (ave) = 2,000 Acid # = 850 | I II | 10 20 | 62 40 |
| 3 | Poly L-Lactide (Commercial) Mw (ave) = 50,000 Acid # = 2100 | I | 10 | 54 |
| 4 | 48/48/4 Poly d,l-Lactide/ Glycolide/1,6 hexanediol (Method III) Acid # = 10,138 $\eta_{inh} = 0.39$ | I | 20 | 43 |
| 5 | 49/49/2 Poly L-Lactic/ Glycolic/Malic Acid (Type 18) Acid # = 1400 $\eta_{inh} = 0.20$ | I I I I I II III | 10 20 30 40 50 20 20 | 100 99 95.5 96.0 99.8 99.8 77.5 |
| 6 | 83.3/14.7/2 Poly L-Lactic/ Glycolic/Citric Acid (Type IA) Acid # = 563 $\eta_{inh} = 0.24$ | I | 20 | 96 |
| 7 | 49/49/2 Poly d,l-Lactide/ | I | 20 | 96 |
| | Glycolide/Malic Acid (Type II) Acid # = 1200 $\eta_{inh} = 0.21$ | III | 20 | 73.9 |
| 8 | 48/48/4 Poly d,l-Lactide/ Glycolide/Citric Acid (Type III) Acid # = 589 $\eta_{inh} = 0.22$ | I | 10 | 90 |

[1]In all cases, conjugates were formed as outlined in text using acetone as solvent and sodium hydroxide as base. All peptides used were in the acetate salt form.
[2]Peptides: I BIM-21003
D-Trp⁶-LHRN(pGlu-His-Trp-Ser-Tyr-D-Trp-Leu-Arg-Pro-Gly NH₂) pks = 10.1
II BIM-23014
(N₂-β-D-Nal-Cys-Tyr-Trp-Lys-Val-Cys-ThrNN₂)
pks = 9.8
III BIM-26226
(H₂N-D-F₅ Phe-Gln-Trp-Ala-Val-D-Ala-His-Leu-OCH₃) pks = 8.0
[3]% Retention: Measured by rinsing the dried polyester/peptide ionic conjugates with D.I. water and quantitating soluble peptide in rinses by HPLC
$$\% \text{ Retention} = 100\% \times \frac{\text{Wt. Peptide Loaded} - \text{Wt. Soluble Peptide}}{\text{Wt. Peptide Loaded}}$$

(3) Conversion of ionic conjugates to implants, rods, microspheres of microparticles, capable of releasing in vivo the therapeutic agent for at least 20 days in a monophasic profile. The ionic conjugate salts of the invention can be converted to: (A) sterile injectable microspheres (with or without 0.1 to 10% of a solid polyhydric alcohol as processing aid) containing 1 to 50% by weight polypeptide that can released according to an essentially monophasic profile and to sustain pharmacological activity over a period of one to 12 weeks; (B) sterile implantable films made by casting, pressing or extrusion with or without a pharmacologically inactive processing aid, and capable of providing a release profile similar to that described in (A) and; (C) sterile injectable rods made by extrusion or pressing, capable of providing a release profile similar to that described in (A).

In-Vitro Release Assay:

Samples of the dried and ground ionic conjugate material weighing 50 mg each were placed in 25 mm diameter scintillation vials A 5 ml aliquot of modified PBS buffer (PBS buffer: 2.87 gm Na₂HPO₄, 0.654 gm NaH₂PO₄, 5.9 gm NaCl, 0.5 gm NaN₃, Q.S. 1.0 Liter with Deionized water; pH=7.27.) was added to each vial and the vials were placed in a Lab.-Line Orbit Environ-Shaker and swirled at 120 R.P.M. and 37° C. Vials were withdrawn periodically and decanted and replenished with fresh PBS solution. The amount of released peptide was determined from the decanted PBS solutions by HPLC.

Peptide Extraction From Ionic Conjugates:

A 50 mg sample of an ionic molecular conjugate was mixed into 20 mls of methylene chloride. The mixture was sequentially extracted with 50 ml, 20 ml and 20 ml portions of 2N acetic acid. The acetic acid extracts were combined and analyzed for peptide content by high performance liquid chromatography (HPLC). Peptide analysis by HPLC is as follows. HPLC analysis were performed using a Waters model M-45 solvent delivery pump and an EM Science MACS 700 detector at wavelength 220 nm and 1.0 AUFS. Peptides were run using a Lichrospher (EM separations) C18,100 Å, 5 μm, 25 cm×4.6 mm column and 30% acetonitrile/0.1% TFA as an isocratic eluent buffer.

Figure 3:
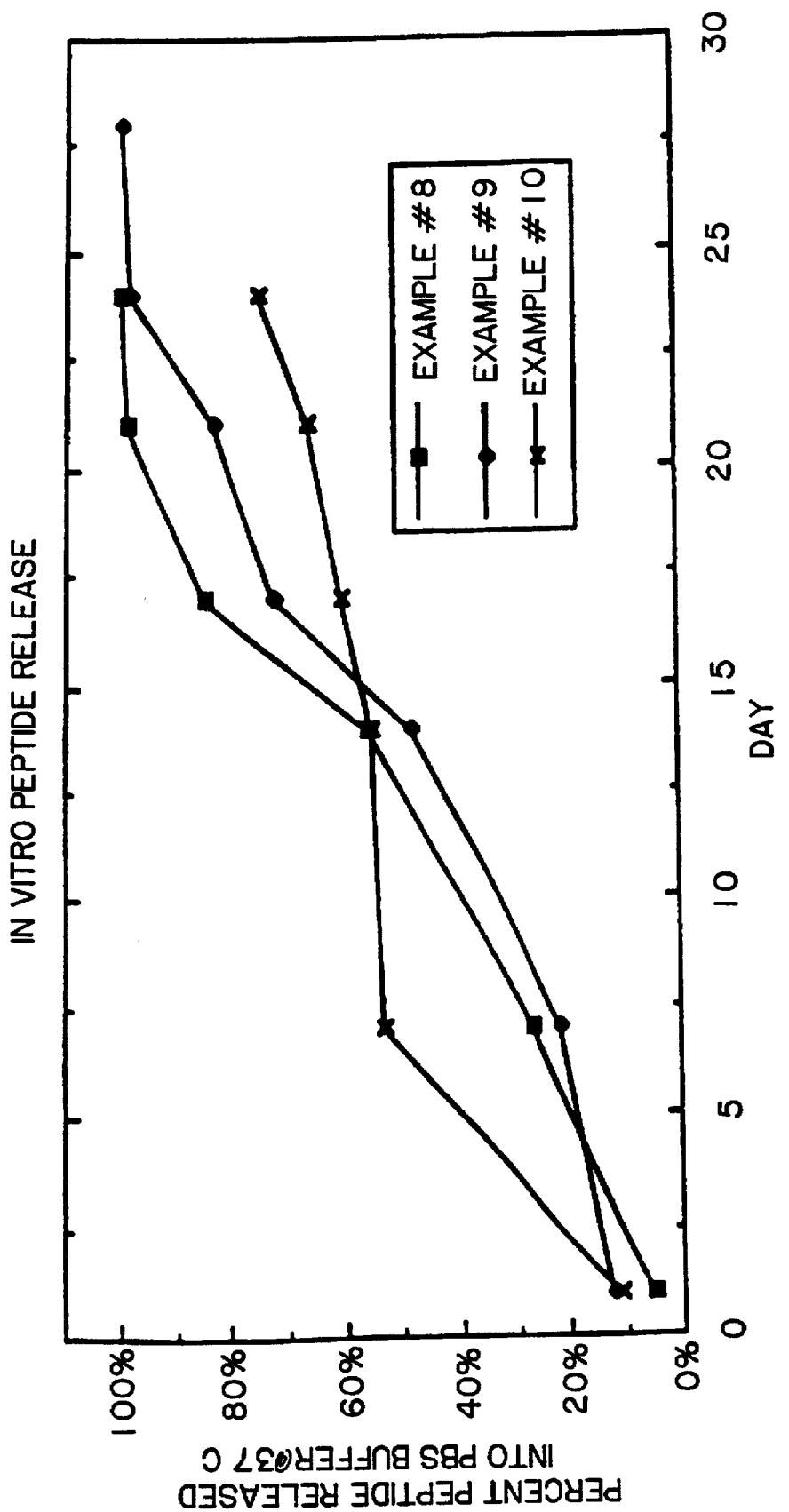
FIG. 3 is a graph depicting the percent peptide released from ionic molecular conjugates into PBS buffer at 37° C. over a 28-day period.

Following are details (Table VI) of the in vitro assay demonstrating the amount of peptide released over a 28 day period for 49:49:2 L-lactic/Glycolic/Malic\D-Trp⁶[LHRH] (Example #8), 49:49:2:L-Lactic/Glycolic/Malic\Somatostatin-Tumor Inhibiting Analogue (Example #9), and 73.5:24.5:2 poly-L-lactide/glycolic/Malic:D-Trp⁶ [LHRH] (Example #10) ionic molecular conjugates. FIG. 3 shows the graphic representation of these data.

TABLE VI

IN-VITRO ASSAY DATA

PERCENT OF TOTAL PEPTIDE RELEASED

| DAY OF ASSAY | Example #8 | Example #9 | Example #10 |
|---|---|---|---|
| 1 | 5.5% | 12.5% | 11% |
| 7 | 26.9% | 21.3% | 53% |
| 14 | 55.2% | 47.3% | 55% |
| 17 | 84.4% | 72.2% | 60% |
| 21 | 98.6% | 82.5% | 66% |
| 24 | 100% | 98.2% | 75% |
| 28 | — | 99.6% | — |

Quantitation of Peptides in Ionic Conjugates

Ionically bound peptides in the conjugate products were measured by dissolving 10 mg samples in 5.7 ml of a 9:1 mixture of acetone and 0.1M aqueous trifluoroacetic acid. The solutions were swirled at 25° for 15–24 hours and then filtered through 0.5 μm teflon filter cartridges. The filtrates were then analyzed for peptide content by high performance liquid chromatography (HPLC). Peptide analysis by HPLC were run using a Millipore model 717 Wisp Autosampler, a model 510 pump and a model 486 UV detector set at 220 nm. Peptides were run on a Lichrospher (EM Separations) 25 cm×4.6 mm C18, 5 μm 100 Å column, flow rate 1.0 ml per minute using 35% acetonitrile in 0.14% sodium perchlorate buffer as an isocratic eluent system. Peptides were quantified by comparison of the area of the correct peak in the sample run with the area of a injected peptide standard. Use Any of the acid-bearing polyesters/polypeptide ionic conjugates described herein can be administered to a recipient alone or in combination with a pharmaceutically-acceptable medium. Although it may be convenient to administer subcutaneously, intramuscularly, parenterally, by suppository or nasally, the therapeutic preparation is administered in accordance with the condition to be treated. The concentration of the composition in the formulations of the invention will vary depending upon a number of issues, including the dosage to be administered, and the route of administration.

Without further elaboration, it is believed that one skilled in the art can, using the preceding description, utilize the instant invention to its fullest extent. The following embodiments are, therefore, to be construed as merely illustrative, and not limitative of the remainder of the disclosure in any way whatsoever.

EXAMPLE 1—DIRECT CONDENSATION METHOD—Sythesis of 50/50 Poly(D,L-Lactic-co-glycolic) catalysed by Amerlyst 15

D,L-lactic acid (85% aqueous mixture; 13.7 μm, 0.13 mole) was mixed with glycolic acid (10 gm, 0.13 mole) was mixed with glycolic acid (10 gm, 0.13 mole) in a round bottom flask fitted with a magnetic stirrer, a Dean-Stark trap and a water cooled condenser. Toluene (100 ml) and Amerlyst 15 beads (100 mg) were added and the mixture was refluxed under nitrogen for 72 Hours, removing water from the mixture. The mixture was cooled, toluene was decanted from the solidified mass and the product was dissolved in methylene chloride (250 ml). The methylene chloride solution was treated with activated charcoal (Darco, 500 mg), filtered and vacuum dried in a rotary evaporator. The polyester was further dried under high vacuum (1 mm Hg) at 40° C. to afford a white powder.

($\eta_{inh}$ in CHCl$_3$=0.3, Acid #=2439, Tg=12° C.)

EXAMPLE 2—DIRECT CONDENSATION METHOD—Synthesis of 49/49/2 Poly(L-Lactic-co-glycolic/citric) catalyzed by Amberlyst 15

Using a system similar to above L-lactic acid (88% aqueous mixture; 25.6 gm, 0.25 mole) was combined with glycolic acid (19.2 gm, 0.25 mole), citric acid monohydrate (2.33 gm, 0.011 mole), Amberlyst 15 beads (500 mg) and toluene (150 ml) in a round bottom flask. The mixture was heated with stirring to reflux for 51 hours, removing water by the Dean-Stark trap. The toluene was decanted from the semi solid product. The polyester was dissolved into acetone (300 ml) and filtered and dried on a rotary evaporator. The solid polyester was then redissolved in methylene chloride and was washed twice with water (2×150 ml) to remove soluble oligomers. The organic solution was concentrated on a rotary evaporator and the product was thoroughly dried under vacuum to afford a white solid (see Table I, Type IB Polyester, Polymer #4).

($\eta_{inh}$ in CHCl$_3$=0.11, Acid #=842, Tg=15° C.)

EXAMPLE 3—STEP GROWTH POLYMERIZATION METHOD Synthesis of 73.5/24.5/2 Poly(L-Lactide-co-glycolic/malic) catalyzed by malic acid.

Using a 150 ml capacity cylindrical ampule with an air impinger fitting L-lactide (20 gm, 0.139 mole) was combined with glycolic acid (7.1 gm, 0.093 mole) and (d,l)-malic acid (1.0 gm, 0.0075 mole). The mixture was agitated by bubbling nitrogen through the impinger inlet (100 ml/min) and heated from 25° C. to 155° C. over 100 minutes. The reaction temperature was maintained at 155° C. for 70 hours and the water from polymerization was removed in a cold trap on the reactor outlet line. After 70 hours the reaction was cooled to 100° C. and poured into a chilled stainless steel receiver for hardening. The solid polyester was then dissolved in methylene chloride and was washed twice with water (2×150 ml) to remove soluble oligomers. The organic solution was concentrated on a rotary evaporator and the product was thoroughly dried under vacuum to afford a white solid (see Table II, Type II Polyester, Polymer #2).

($\eta$inh in CHCl$_3$=0.13, Acid #=1800, Tg=27° C.)

EXAMPLE 4—RING OPENING POLYMERIZATION METHOD—Synthesis of 75/25 poly(L-lactide-co-glycolide) initiated by malic acid.

L-lactide (12.0 g, 0.0833 mole), glycolide (3.21 g, 0.0277 mole), malic acid 0.3042 g, 0.00227 mole), and stannous octoate catalyst (0.33M in toluene, 67 μL, 0.022 mmole) were added under dry nitrogen conditions to a glass ampule with a magnetic stirrer. The system was purged with N$_2$ and evacuated with vacuum several times before sealing the ampule. The reactants were then melted at 140° C. and the melt was heated at 180°, 190°, 180°, and 150° for 1, 4.5, 12, and 2 hours, respectively. After cooling to room temperature, the polyester was reheated to 110° C. under a vacuum of less than 1 mm Hg for about one hour to remove monomer, recooled at room temperature, quenched in liquid nitrogen, isolated and dried under vacuum ($\eta_{inh}$ in $CHCl_3$=0.20, Acid #=2560, $T_g$=39° C.)

EXAMPLE 5—RING OPENING POLYMERIZATION METHOD—Synthesis of 50/50 poly(D,L-lactide-co-glycolide) initiated by citric acid.

D,L-lactide (10.0 g, 0.0694 mole) was mixed with glycolide (8.06 g, 0.0694 mole), citric acid (1,07 g, 0.00555 mole) and stannous octoate catalyst (0.33M in toluene, 84 μL, 0.0278 mmole) under a dry nitrogen atmosphere in a glass ampule containing a magnetic stirrer and sealed under vacuum. The reactants were melted and heated at 180°, 185°, 195° and 120° C. for 1, 2, 7, and 9 hours, respectively. The polyester was cooled to room temperature, quenched in liquid nitrogen, isolated, and dried.

($\eta_{inh}$ in $CHCl_3$=0.26, Acid #=970, $T_g$=23° C.)

EXAMPLE 6—RING OPENING POLYMERIZATION METHOD—Sythesis of 50/50 poly(D,L-lactide-co-glycolide) initiated by 1,6-hexanediol.

Using a system similar to those described above, D,L-lactide (10.0 g, 0.0694 mole), glycolide (8.06 g, 0.0694 mole), 1,6-hexanediol (0.656 g, 0.00555 mole), and stannous octoate (0.33M in toluene, 84 μL, 0.0278 mmole) were added under dry nitrogen conditions to a glass ampule which was subsequently sealed under vacuum. The constituents were heated at 150°, 185°, 150°, and 120° C. for 0.5, 4, 1, 5, and 3 hours, respectfully. The resulting polyester was recovered and dried (see Table III, Type III Polyester, Polymer #5).

($\eta$inhin $CHCl_3$=0.39, Acid #=10,138, $T_g$=30° C.)

EXAMPLE 7—FUNCTIONAL INTERCHANGE METHOD—Synthesis of carboxylic-bearing 50/50 poly(D,L-lactide-co-glycolide).

50/50 poly(D,L-lactide-co-glycolide) (Boehringer A001, 8 g), citric acid (0.8 g, 4.16 mmole), and stannous octoate (2 drops) were added to a glass ampule under dry nitrogen conditions and sealed. The mixture was heated at 150° for 4 hours, cooled to room temperature, quenched in liquid nitrogen, isolated, and dried (see Table IV, Type IV Polyester, Polymer #1).

($\eta_{inh}$ in $CHCl_3$=0.26, Acid #=670, $T_g$=23 C.)

EXAMPLE 8—Synthesis of a 49:49:2 L-Lactic/Glycolic/Malic (See Table I, Polymer #4) and D-Trp$^6$ [LHRH] ionic molecular conjugate.

500 mg of 49:49:2 L-lactic/Glycolic/Malic (synthesized by direct condensation; Mw=9,500; Acid #=1420) was dissolved in 10 mls of Acetone (Mallinckrodt Analytic Reagent). A portion of 0.1N sodium hydroxide solution (1.14 ml) was added and the mixture was stirred at room temperature for 15 minutes. A solution of 100 mg of D-Trp$^6$ [LHRH] (BIM-21003 Peptide I; base content 87%, acetate content 7%) in 1.0 ml water was added and the mixture was stirred for i hour at room temperature. The solvents were then removed, first by Rotovap at T<40° C. and then in a desiccator for 1 hour at room temperature under 1 mm Hg vacuum. The dried solid was triturated and stirred in 100 mls of deionized Water and isolated by filtration. The aqueous filtrate was tested by HPLC and found to contain <1 mg soluble peptide. The solid material was dried several days in vacuo to give 540 mg of white powder. The powder was used in an in vitro assay (see Table VI, Example #e).

EXAMPLE 9—Synthesis of a 49:49:2 L-lactic/glycolic/malic, see Table I, polymer #4) and Somatostatin/Tumor Inhibiting Analogue ionic molecular conjugate.

100 mg of 49:49:2 L-Lactic/Glycolic/Malic (synthesized by direct condensation; Mw=9,500; Acid #=1420) was dissolved in 2 mls of acetone (Mallinckrodt Analytic Reagent). A portion of 0.1N sodium hydroxide solution (0.32 ml) was added and the mixture was stirred at room temperature for 15 minutes. A solution of 20 mg of Somatostatin/Tumor Inhibiting Analogue (BIM-23014 Peptide II; base content 83%, acetate content 9.8%) in 1.2 ml water was added and the mixture was stirred for 1 hour at room temperature. The solvents were then removed, first by Rotovap at T<40° C. and then in a desiccator for 1 hour at room temperature under 1 mm Hg vacuum. The dried solid was triturated and stirred in 20 mls of Deionized Water and isolated by filtration. The aqueous filtrate was tested by HPLC and found to contain <0.05 mg soluble peptide. The solid material was dried several days in vacuo to give 106 mg of white powder. The powder was ground and used in an in vitro release assay (see Table VI, Example #9).

EXAMPLE 10—Synthesis of a 73.5:24.5:2 poly L-lactide/glycolic/malic (see Table II, see polymer #2) and D-Trp$^6$ [LHRH] ionic molecular conjugate.

800 mg of 73.5:24.5:2 poly L-lactide/glycolic/malic (synthesized by step growth of acylized products; Acid #=1800) was dissolved in acetone (16 ml). A portion of 0.1N sodium hydroxide solution (2.8 ml) was added and the solution was stirred at room temperature for 20 minutes. A solution of 200 mg of D-Trp$^6$ [LHRH] (BIM-21003; base content 87%, acetate content 7%) in 2 ml water, was added and the mixture was stirred for 90 minutes. The solvents were removed and the resulting solid was triturated in deionized water as in Example 8 indicating less than 1% soluble peptide salt present. The isolated solids were dried 4 days in vacuo to give 839 mg of white powder. The powder was ground and used for in vitro release assay (see Table VI, Example #10).

EXAMPLE 11—Formation of peptide-polymer Ionic Conjugate Microparticle 1.50 of L-lactide/glycolide/d,l malic acid polyester (65; 33; 2).

Conjugates were synthesized by ring opening polymerization as in example 4 (MW=4700 polydispersity=1.3 as determined by GPC on a Jordi Gel 50×1 cm mixed linear bed column, THF eluent, Wyatt Mini Dawn light scattering detector dn/dc =0.05, acid #1475 by titration, $T_g$=42° C.], was dissolved in 40 ml of acetone. The acid groups were neutralized with 2.0 ml of 0.5 g of BIM-23014 (peptide content 83.7%, acetate content 11.5%) in 20 ml of Milli-Q water was slowly added with mixing to the polymer solution. An additional 40 ml of acetone was also added portionwise during the peptide addition to prevent precipitation. The clear, colorless solution was stirred for one hour and then evaporated to dryness under vacuum. The resulting white solid was redissolved in a mixture of 20 ml of acetone and 2 ml of Milli-Q water to form a clear solution. This solution was injected, via a 0.2 μ teflon filter into a rapidly stirring reservoir of 500 ml Milli-Q water at 4° C. The polymer/peptide complex phase separated immediately into small particles upon contact with the water. After mixing the slurry for 30 min at 4°, the residual acetone was removed under reduced pressure and the solids were isolated by centrifugation, resuspended with 100 ml of Milli-Q water, and recentrifuged. The isolated solids were dried by lyophilization to give 1530 mg of white free flowing powders. Particles size range=2–100 μm. The $T_g$ of the ionic conjugate was shown to occur at 53° C. Total residual (unbound) peptide in all aqueous supernatents was found to be 63 mg by HPLC analysis. The total initial peptide content was determined by elemental nitrogen analysis to be 19.9% by weight. The percentage of extractable peptide from the conjugate was determined to be 16.9%, by weight, using the acetone/0.1M TFA extraction technique. The resulting conjugate, thus, retains 84.8% ionic (extractable) character.

From the foregoing description, one skilled in the art can easily ascertain the essential characteristics of this invention, and without departing from the spirit and scope thereof, can make various changes and modifications of the invention to adapt it to various usages and conditions. Thus, other embodiments are also within the claims.

What is claimed is:

1. A composition comprising a polyester containing one or more free COOH groups ionically conjugated with a bioactive polypeptide comprising at least one effective ionogenic amine, wherein said polyester contains a member selected from the group of L-lactic acid, D-lactic acid, DL-lactic acid, ε-caprolactone, p-dioxanone, ε-caproic acid, alkylene oxalate, cycloalkylene oxalate, alkylene succinate, β-hydroxybutyrate, substituted or unsubstituted trimethylene carbonate, 1,5-dioxopan-2-one, 1,4-dioxepan-2-one, glycolide, glycolic acid, L-lactide, D-lactide, DL-lactide, meso-lactide, and any optically active isomers, racemates or copolymers thereof, and at least 50%, by weight, of the polypeptide present in said composition is ionically conjugated to said polyester.

2. The composition of claim 1, wherein said polyester has a carboxyl to hydroxyl ratio greater than one.

3. The composition of claim 1, wherein said polyester is composed of a member chosen from the group of L-lactic acid, D-lactic acid; DL-lactic acid; ε-caprolactone; p-dioxanone; ε-caproic acid; substituted or unsubstituted trimethylene carbonate; glycolide; glycolic acid; L-lactide; D-lactide; DL-lactide; meso-lactide; and any optically active isomers; racemates or copolymers thereof.

4. The composition of claim 1, wherein said polyester is partially acid-tipped with glutaric anhydride.

5. The composition of claim 1, wherein said polyester is fully acid-tipped with glutaric anhydride.

6. The composition of claim 1, wherein said polyester has an average degree of polymerization between 10 and 300.

7. The composition of claim 1, wherein said polyester has a viscosity of about 0.05— to about 0.7 dl/g in chloroform and an average molecular weight of about 1200–40,000.

8. The composition of claim 1, wherein said bioactive polypeptide comprises 1 to 50 percent of total weight of said ionic molecular conjugate.

9. The composition of claim 1, wherein greater than 85% of said polypeptide present in said composition is ionically conjugated to said polyester.

10. The composition of claim 1, wherein said polypeptide is chosen from the group consisting of LHRH, somatostatin, bombesin/GRP, calcitonin, bradykinin, galanin, MSH, GRF, amylin, tachykinins, secretin, PTH, CGRP, neuromedins, PTHrP, glucagon, neurotensin, ACTH, GHRP, GLP, VIP, PACAP, enkaphelin, PYY, motilin, substance P, NPY, TSH, an analog thereof, and a fragment thereof.

11. The composition of claim 1, wherein said ionic conjugate is capable of releasing in vivo a therapeutically effective dose of said polypeptide over a period of at least 7 days.

12. A method of synthesizing a composition comprising (a) providing a polyester and a bioactive polypeptide having at least one effective ionogenic amine, wherein said polyester contains a member selected from the group of L-lactic acid, D-lactic acid, DL-lactic acid, ε-caprolactone, p-dioxanone, ε-caprolic acid, alkylene oxalate, cycloalkylene oxalate, alkylene succinate, β-hydroxybutyrate, substituted or unsubstituted trimethylene carbonate, 1,5-dioxopan-2-one, 1,4-dioxepan-2-one, glycolide, glycolic acid, L-lactide, D-lactide, DL-lactide, meso-lactide, and any optically active isomers, racemates or copolymers thereof, and (b) ionically conjugating said polyester to said polypeptide to form an ionic molecular conjugate in which the polypeptide is ionically conjugated to the polyester.

13. The method of claim 12, wherein at least 50%, by weight, of the polypeptide present in the composition is ionically conjugated to the polyester.

14. The method of claim 13, wherein said polyesters possess acid-tipped hydroxyl end groups.

15. The method of claim 14, wherein said hydroxyl end groups are partially acid-tipped with glutaric anhydride.

16. The method of claim 14, wherein said hydroxyl end groups are fully acid-tipped with glutaric anhydride.

17. The method of claim 13, wherein said polyesters are synthesized using hydroxy polycarboxylic acids chain initiators.

18. The method of claim 13, wherein the hydroxyl endgroups of said polyesters are acid-tipped.

19. The method of claim 18, wherein said hydroxyl end-groups are partially acid-tipped with glutaric anhydride.

20. The method of claim 18, wherein said hydroxyl end-groups are fully acid-tipped with glutaric anhydride.

21. The method of claim 13, wherein the synthesis of said polyester results in an average degree of polymerization between 10 and 300.

22. The method of claim 21, wherein said polyester has a carboxyl to hydroxyl end group ratio greater than one.

23. The method of claim 13, wherein synthesizing said polyester/polypeptide ionic molecular conjugate comprises: (a) dissolving the polyester in tetrahydrofuran, acetone, or ethylene glycol dimethylether followed by adding a base; and (b) adding an aqueous solution of a polypeptide or salt of a polypeptide at polypeptide/polyester loading levels of 2% to 50% w/w (polypeptide/polyester).

24. The method of claim 23, wherein said polypeptide is a salt of an acid having a pKa greater than or equal to 3.5.

25. The method of claim 23, wherein said polypeptide comprises 1 to 50 percent by total weight of said ionic conjugate.

26. The method of claim 23, wherein greater than 85% of the said polypeptide present in said composition is ionically conjugated to said polyester.

27. The method of claim 23, wherein said reaction results in the formation of an ionic bond between said reactants.

28. A composition made by the process of claim 12.

29. A method of synthesizing a microparticle comprising (a) dissolving the composition of claim 1 in an aprotic, water miscible organic solvent; (b) mixing said organic solvent in water; and (c) isolating said microparticles from said water.

30. The method of claim 29, wherein said organic solvent is chosen from the group consisting of acetone, acetonitrile, tetrahydrofuran, dimethylformamide, and dimethyoxy ethylene glycol.

31. A composition of claim 3, wherein said polypeptide is somatostatin or an LHRH analog.

32. A composition of claim 31, wherein said peptide is of the formula pGlu-His-Trp-Ser-Tyr-D-Trp-Leu-Arg-Pro-Gly-$NH_2$ or β-D-Nal-Cys-Tyr-D-Trp-Lys-Val-Cys-Thr-$NH_2$.

* * * * *